United States Patent
Watanabe et al.

(10) Patent No.: US 11,058,290 B2
(45) Date of Patent: Jul. 13, 2021

(54) ENDOSCOPE APPARATUS HAVING A PLURALITY OF HEAT GENERATORS AND CORRESPONDING AIR FLOW PATHS

(71) Applicant: OLYMPUS CORPORATION, Tokyo (JP)

(72) Inventors: Masaaki Watanabe, Hachioji (JP); Tatsuya Nakanishi, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 406 days.

(21) Appl. No.: 16/037,353

(22) Filed: Jul. 17, 2018

(65) Prior Publication Data

US 2018/0317759 A1 Nov. 8, 2018

Related U.S. Application Data

(63) Continuation of application No. PCT/JP2017/010989, filed on Mar. 17, 2017.

(30) Foreign Application Priority Data

Apr. 4, 2016 (JP) .............................. JP2016-075370

(51) Int. Cl.
*A61B 1/06* (2006.01)
*A61B 1/12* (2006.01)
(Continued)

(52) U.S. Cl.
CPC ................ *A61B 1/12* (2013.01); *A61B 1/05* (2013.01); *A61B 1/06* (2013.01); *A61B 1/0669* (2013.01);
(Continued)

(58) Field of Classification Search
None
See application file for complete search history.

(56) References Cited

U.S. PATENT DOCUMENTS 5,544,012 A * 8/1996 Koike ................ H05K 7/20572
361/695
6,222,729 B1 * 4/2001 Yoshikawa ........ H05K 7/20154
174/16.1
(Continued)

FOREIGN PATENT DOCUMENTS

CN 103079386 A 5/2013
EP 2015137 A2 1/2009
(Continued)

OTHER PUBLICATIONS

International Search Report dated Jun. 20, 2017 issued in PCT/JP2017/010989.

*Primary Examiner* — John P Leubecker
(74) *Attorney, Agent, or Firm* — Scully, Scott, Murphy & Presser, P.C.

(57) ABSTRACT

An endoscope apparatus includes: a housing; a first heat generator disposed in the housing; an air feeding unit disposed in the housing and configured to cause air to pass in a vicinity of the first heat generator; a second heat generator disposed in the housing and provided in one of places above and below a flow path for the air, caused by the air feeding unit to pass in the vicinity of the first heat generator, in a height direction of the housing; and a guide plate provided on the flow path for the air, caused by the air feeding unit to pass in the vicinity of the first heat generator, and having an inclination for changing the flow path for the air after passage in the vicinity of the first heat generator to another of the places above and below in the height direction of the housing.

5 Claims, 10 Drawing Sheets

(51) Int. Cl.
  *G02B 23/24* (2006.01)
  *A61B 1/05* (2006.01)
  *A61B 8/13* (2006.01)
(52) U.S. Cl.
  CPC .......... *A61B 1/128* (2013.01); *G02B 23/2476* (2013.01); *G02B 23/2484* (2013.01); *A61B 8/13* (2013.01)

(56) References Cited

U.S. PATENT DOCUMENTS

| | | | | |
|---|---|---|---|---|
| 6,224,248 B1* | 5/2001 | Chiba | ................ | G03F 7/70016 362/373 |
| 7,551,436 B2* | 6/2009 | Hata | ................ | H05K 7/20563 324/502 |
| 7,752,858 B2* | 7/2010 | Johnson | ............ | H05K 7/20836 62/186 |
| 7,952,869 B2* | 5/2011 | Lewis, II | ................ | H05K 7/20 361/695 |
| 9,202,773 B2* | 12/2015 | Bae | ....................... | H01L 23/467 |
| 9,497,891 B2* | 11/2016 | Alvarado | ........... | H05K 7/20736 |
| 2013/0100610 A1* | 4/2013 | Schneider | ......... | H05K 7/20145 361/690 |
| 2016/0235285 A1* | 8/2016 | Shirota | ................ | G02B 27/141 |
| 2016/0353984 A1* | 12/2016 | Shirota | ................. | A61B 1/128 |

FOREIGN PATENT DOCUMENTS

| | | | |
|---|---|---|---|
| EP | 3090679 A1 | 11/2016 | |
| JP | H04-108422 A | 4/1992 | |
| JP | H06-22908 A | 2/1994 | |
| JP | 2000-102504 A | 4/2000 | |
| JP | 2006-075308 A | 3/2006 | |
| JP | 2008-286915 A | 11/2008 | |
| JP | 2016-015995 A | 2/2016 | |
| WO | WO-2015064470 A1 * | 5/2015 | ......... G02B 23/2461 |
| WO | WO 2015/178054 A1 | 11/2015 | |

* cited by examiner

ENDOSCOPE APPARATUS HAVING A PLURALITY OF HEAT GENERATORS AND CORRESPONDING AIR FLOW PATHS

CROSS REFERENCE TO RELATED APPLICATION

This application is a continuation application of PCT/JP2017/010989 filed on Mar. 17, 2017 and claims benefit of Japanese Application No. 2016-075370 filed in Japan on Apr. 4, 2016, the entire contents of which are incorporated herein by this reference.

BACKGROUND OF THE INVENTION

1. Field of the Invention

The present invention relates to an endoscope apparatus including a plurality of heat generators.

2. Description of the Related Art

An electronic endoscope is used by being connected to an endoscope apparatus that performs image processing on an image picked up by the electronic endoscope, for example as disclosed in Japanese Patent Application Laid-Open Publication No. 2016-15995.

SUMMARY OF THE INVENTION

An endoscope apparatus according to one aspect of the present invention includes: a housing; a first heat generator disposed in the housing and configured to generate heat; an air feeding unit disposed in the housing and configured to cause air for cooling the first heat generator to pass in a vicinity of the first heat generator; a second heat generator disposed in the housing and provided in one of places above and below a flow path for the air, caused by the air feeding unit to pass in the vicinity of the first heat generator, in a height direction of the housing; and a guide plate provided on the flow path for the air, caused by the air feeding unit to pass in the vicinity of the first heat generator, and having an inclination for changing the flow path for the air after passage in the vicinity of the first heat generator to another of the places above and below in the height direction of the housing.

DETAILED DESCRIPTION OF PREFERRED EMBODIMENTS

Figure 1:
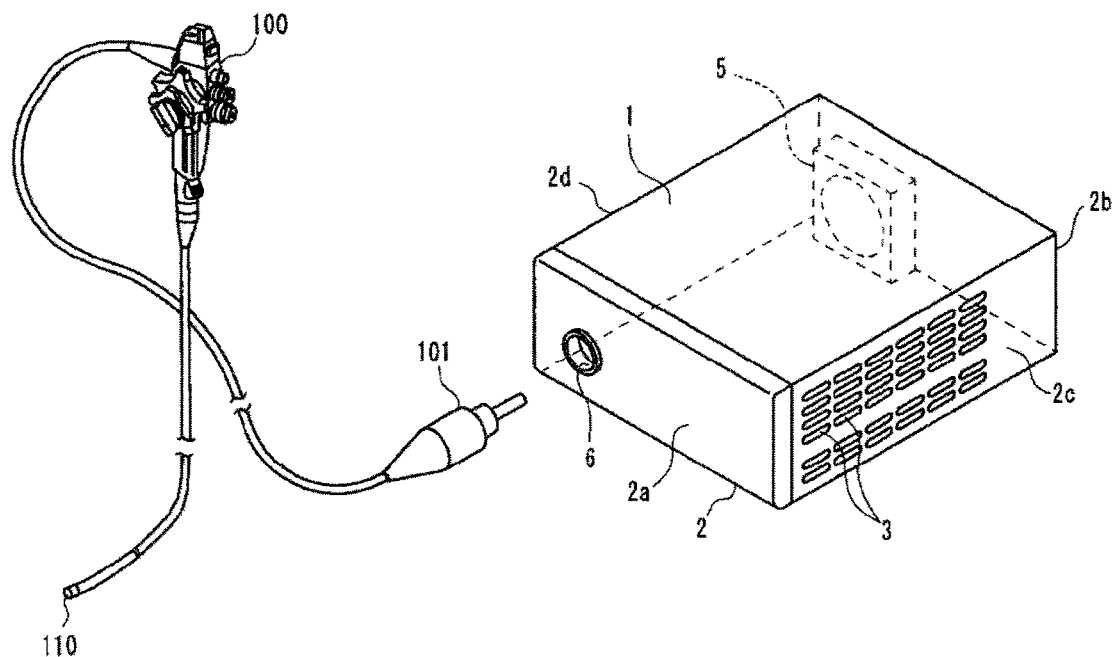
FIG. 1 is a perspective view showing a front surface side of an endoscope apparatus.

Preferred embodiments of the present invention will be described below with reference to the drawings. In each of the drawings to be used in the following description, each component is made different in scale so as to have a size recognizable in the drawing, and the present invention is not limited only to quantities of the components, shapes of the components, size ratios of the components, and relative positional relationships among the components, which are described in the drawings.

In the following description, "above" represents a position which is more distant from a ground than a comparison target is, and "below" represents a position which is closer to the ground than the comparison target is. In addition, "high and low" in the following description represent a height relationship along a gravity direction.

First Embodiment

Figure 2:
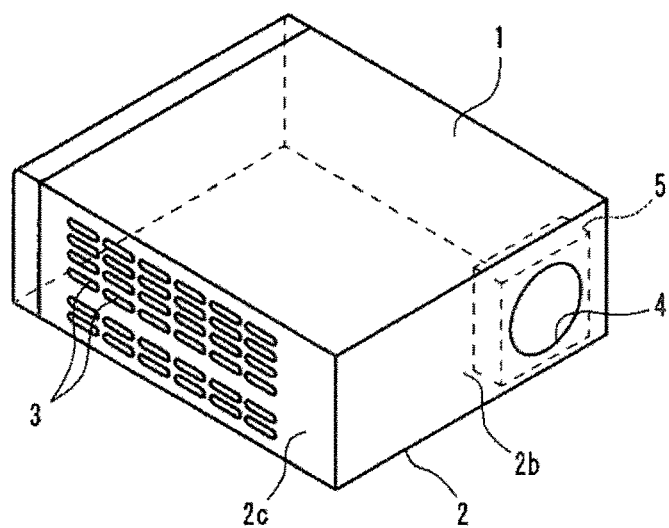
FIG. 2 is a perspective view showing a rear surface side of the endoscope apparatus.

An endoscope apparatus 1 of the present embodiment shown in FIGS. 1 and 2 is an electronic device that is used together with an endoscope 100. The endoscope apparatus 1 can communicate with an image pickup apparatus 110 included in the endoscope 100 by wired or wireless means, and includes an electronic circuit configured to generate an observed image based on a signal inputted from the image pickup apparatus 110 and to output the generated image to an image display apparatus, not shown.

The image pickup apparatus 110 of the endoscope 100 which is used together with the endoscope apparatus 1 of the present embodiment has a configuration to pick up one of or both an optical image and an ultrasound tomographic image of a subject. A configuration of the endoscope 100 is known, so that detailed description of the configuration will be omitted.

In the present embodiment, as one example, the endoscope apparatus 1 includes a connector portion 6 connectable to a plug-shaped connector 101 included in the endoscope 100. The electronic circuit of the endoscope apparatus 1 is electrically connected to the image pickup apparatus 110 of the endoscope 100 via the connector portion 6 to control operation of the image pickup apparatus 110 and supply power to the image pickup apparatus 110.

A housing 2 of the endoscope apparatus 1 has a shape of a rectangular parallelepiped box and accommodates inside a plurality of heat generators constituting the electronic circuit and the like. In a state where the endoscope apparatus 1 is mounted in a usable posture on a plane substantially parallel to the ground, the connector portion 6 is disposed on one surface upright on the ground. In the following description, the surface on which the connector portion 6 is disposed is referred to as a front surface 2a. A surface on the opposite side of the housing 2 from the front surface 2a is referred to as a rear surface 2b, and a right-side side surface and a left-side side surface, with the front surface 2a located just in the front, are referred to as a left side surface 2c and a right side surface 2d, respectively.

The left side surface 2*c* of the housing 2 is formed with an inlet 3 configured to communicatively connect the inside and the outside of the housing 2. The rear surface 2*b* of the housing 2 is formed with an outlet 4 configured to communicatively connect the inside and the outside of the housing 2.

The endoscope apparatus 1 causes air, taken in from the outside to the inside of the housing 2 through the inlet 3, to pass in the housing 2 and thereafter exhausts the air to the outside from the outlet 4 so as to discharge heat, generated by a plurality of aftermentioned heat generators disposed inside the housing 2, to the outside of the apparatus and cool the heat generator. A detail of a flow path for the air inside the housing 2 will be described later.

In the present embodiment, as one example, an exhaust fan 5 is disposed at the outlet 4, and operation of the exhaust fan 5 generates a flow of air outside the housing 2 so as to pass inside the housing 2. Note that the configuration to generate the flow of the air outside the housing 2 so as to pass inside the housing 2 is not particularly limited, and a fan may be provided at the inlet 3, for example. In addition, as described later, an air feeding unit 20 configured to cause air to flow and move is installed inside the housing 2 in addition to the exhaust fan 5.

Figure 3:
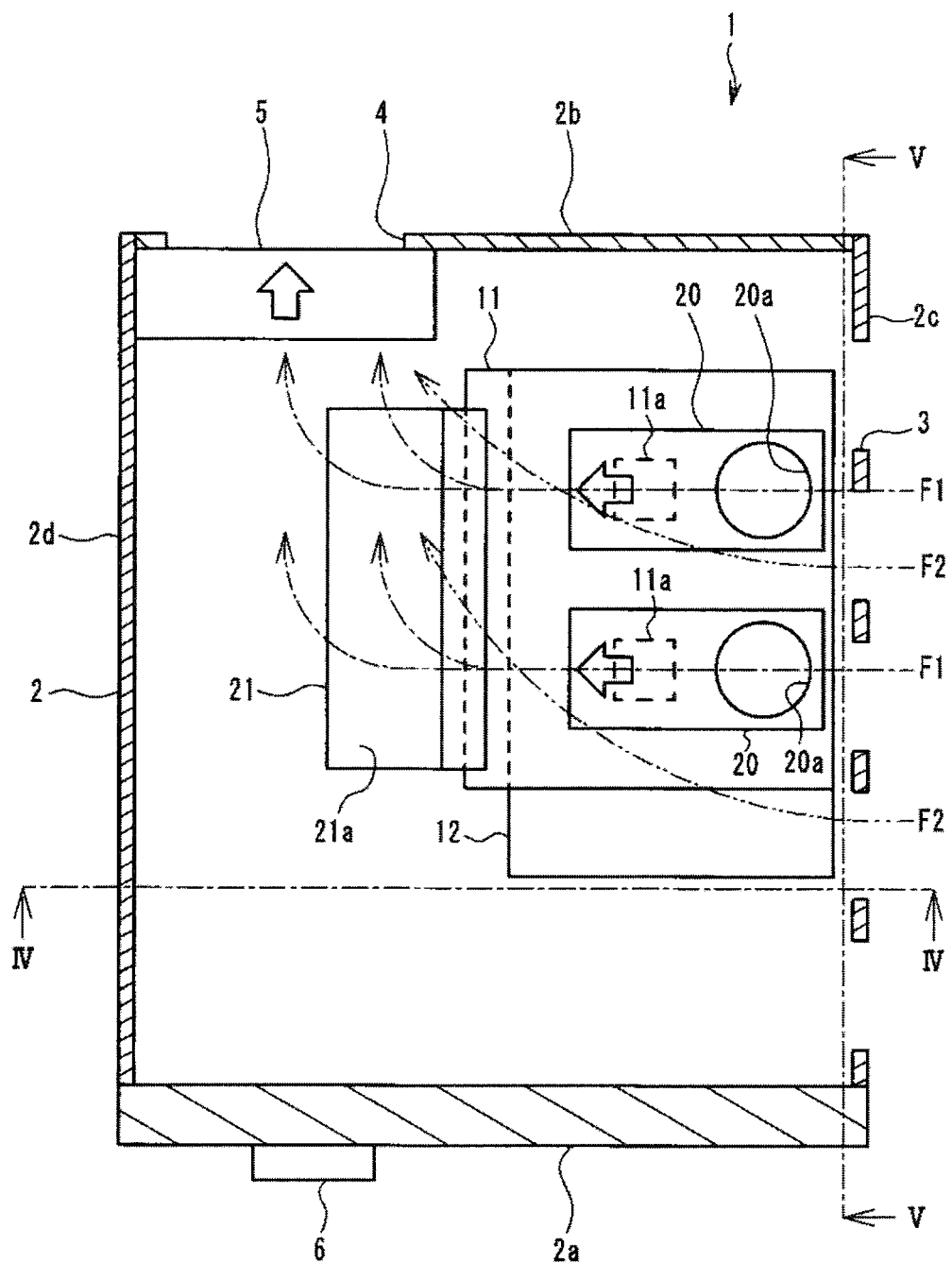
FIG. 3 is a view of an inside of a housing in a first embodiment, seen from above.
Figure 4:
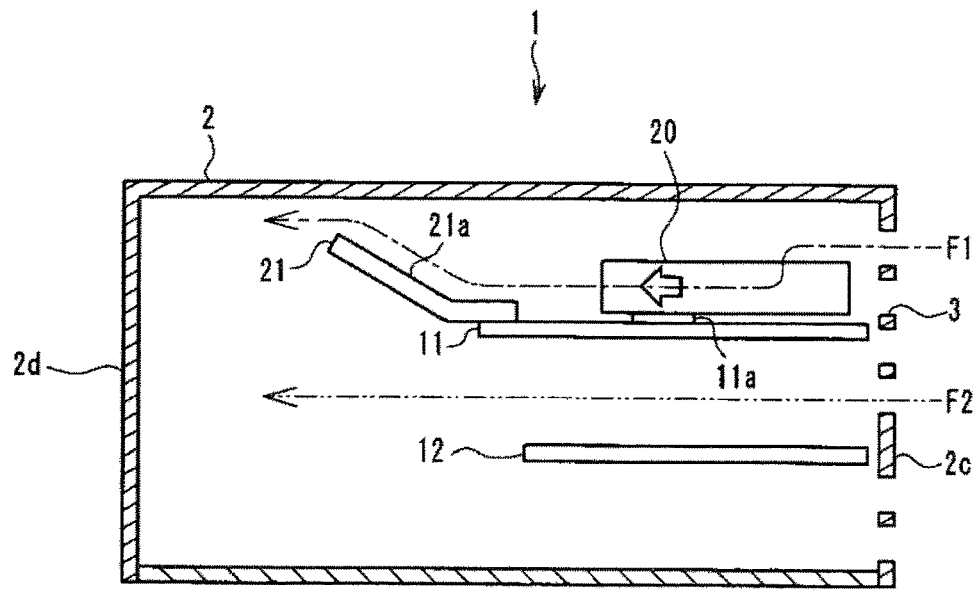
FIG. 4 is a sectional view taken along IV-IV of FIG. 3.
Figure 5:
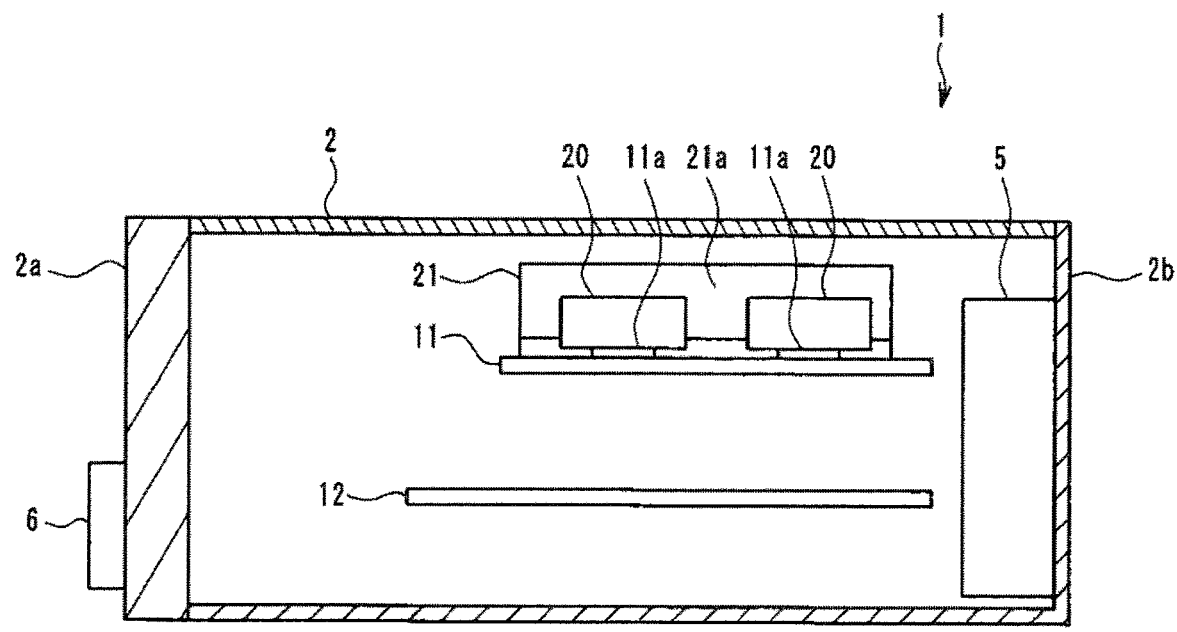
FIG. 5 is a sectional view taken along V-V of FIG. 3.

Next, placement of the heat generator and a shape of the flow path for the air inside the housing 2 will be described. FIG. 3 is a view of the inside of the housing 2 seen from above. In FIG. 3, a lower part of the figure is the front surface 2*a* side. FIG. 4 is a sectional view taken along IV-IV of FIG. 3. FIG. 5 is a sectional view taken along V-V of FIG. 3. In each of FIGS. 4 and 5, the gravity is directed to a lower part of the figure.

As shown in FIG. 3, the inlet 3 is made up of a plurality of through holes arranged on almost the entire left side surface 2*c* in horizontal and height directions. Note that the inlet 3 may be in a form of being made up of a single through hole and provided with a mesh member.

The outlet 4 is disposed at a position on the rear surface 2*b*, which is closer to the right side surface 2*d* than a center of the rear surface 2*b* is. More specifically, the outlet 4 is disposed in a vicinity of a corner of the rear surface 2*b*, which intersects with the right side surface 2*d*. That is, the outlet 4 is disposed in an end portion of the rear surface 2*b* which is more distant from the left side surface 2*c*. Note that the outlet 4 may be made up of a single through hole or may be made up of a plurality of through holes.

A first heat generator 11, a second heat generator 12, an air feeding unit 20, and a guide plate 21 are installed inside the housing 2.

The first heat generator 11 and the second heat generator 12 are members configured to generate heat during operation of the endoscope apparatus 1. In the present embodiment, as one example, the first heat generator 11 and the second heat generator 12 are substrates on which electronic circuits are formed. Note that the first heat generator 11 and the second heat generator 12 are not limited to the substrates. For example, each of the first heat generator 11 and the second heat generator 12 may be a light source apparatus such as an LED or a member configured to generate heat such as an electric motor or may be a member such as a heat sink, through which heat generated by another member conducts.

Inside the housing 2, the first heat generator 11 and the second heat generator 12, which are the substrates, are disposed separately from each other in different positions in a height direction in such postures as to have main surfaces substantially horizontal to each other. Further, the first heat generator 11 and the second heat generator 12 are disposed in such positions as to at least partially overlap with each other in the height direction of the housing in order to at least partially overlap when seen from above. That is, the second heat generator 12 is disposed either above or below the first heat generator 11. In the present embodiment, the first heat generator 11 is disposed so as to cover the second heat generator 12 from above.

Here, a quantity of heat generated by the first heat generator 11 during heat generation is larger than a quantity of heat generated by the second heat generator 12. In the present embodiment, the first heat generator 11 is a substrate mounted with a processor 11*a* configured to perform image processing on an image picked up by the image pickup apparatus 110. The processor 11*a* is mounted on the main surface of the first heat generator 11 which faces upward.

The air feeding unit 20 is disposed in the housing and includes a fan configured to cause air to flow and move such that the air passes in a vicinity of the first heat generator 11 which generates a larger quantity of heat. In the present embodiment, as one example, the air feeding unit 20 includes a centrifugal fan and feeds air toward a heat sink disposed on the processor 11*a*. Here, a direction in which the air feeding unit 20 feeds air is a substantially horizontal direction along the main surface of the first heat generator 11, on which the processor 11*a* is mounted, and is a direction substantially orthogonal to the left side surface 2*c* of the housing 2. An inlet portion 20*a* of the air feeding unit 20 is disposed at a position which is closer to the inlet 3 of the housing 2 than the processor 11*a* is.

By operation of the air feeding unit 20, a first flow path F1 is generated in the housing 2, which is a flow path for air that passes in the substantially horizontal direction in a vicinity of a place above the first heat generator 11. In FIGS. 3 and 4, the first flow path F1 is indicated by an arrow of a one-dot chain line. As shown in FIG. 3, when seen from above, the first flow path F1 is in the direction substantially orthogonal to the left side surface 2*c* in a vicinity of the air feeding unit 20, but as going downstream and getting more distant from the air feeding unit 20, the first flow path F1 is bent in a direction approaching the outlet 4 provided on the rear surface 2*b*.

By the air flowing through the first flow path F1, the heat generated by the first heat generator 11 is discharged outside the housing 2 through the exhaust fan 5 and the outlet 4, and the first heat generator 11 is thus cooled.

Note that two air feeding units 20 and two processors 11*a* are disposed inside the housing 2 in the present embodiment shown, but the number of air feeding units 20 and the number of processors 11*a* may be one or may be three or larger. Further, the air feeding unit 20 may be in a form of including an axial fan.

As described above, the second heat generator 12 is disposed below the first heat generator 11. Hence the second heat generator 12 is disposed below the first flow path F1 lying above the first heat generator 11.

The guide plate 21 is one or a plurality of plate members disposed downstream from the first heat generator 11 on the first flow path F1, through which the air for cooling the first heat generator 11 passes. The guide plate 21 causes the first flow path F1 to bend toward the other side being opposite in the height direction to one side on which the second heat generator 12 is disposed. In other words, the guide plate 21 changes the direction of the first flow path F1 such that the first flow path F1 gets more distant in the height direction from a height, at which the second heat generator 12 is disposed, as going downstream.

In the present embodiment, with the second heat generator 12 disposed below the first flow path F1, the guide plate 21 bends the first flow path F1 upward. More specifically, as shown in FIG. 4, the guide plate 21 is a plate member disposed below the first flow path F1, and an upper surface 21a of the guide plate 21 is an inclined surface that becomes higher as the first flow path F1 goes downstream.

In other words, the upper surface 21a of the guide plate 21 is an inclined surface disposed on the downstream of the air, fed by the air feeding unit 20, from the air feeding unit 20 and changes a flowing and moving direction of the air fed from the air feeding unit 20 upward.

The endoscope apparatus 1 of the present embodiment described above includes, inside the housing 2, the first heat generator 11 and the second heat generator 12 which are a plurality of heat generators. The first heat generator 11 and the second heat generator 12 are substrates disposed so as to at least partially overlap with each other in the height direction. The air feeding unit 20, configured to cause the air to flow and move along the first flow path F1 being along the upper surface of the first heat generator 11, is disposed above the first heat generator 11 that has a larger quantity of heat.

On the downstream of the first flow path F1 from the first heat generator, the guide plate 21 is provided to bend the first flow path F1 toward the other side being opposite to one side in the height direction on which the second heat generator 12 is disposed.

Hence in the present embodiment, the first flow path F1 is made more distant in the height direction from the second heat generator 12 downstream from the first heat generator, whereby it is possible to prevent high-temperature air, which flows through the first flow path F1 after cooling the first heat generator 11, from flowing into a periphery of the second heat generator 12 and to prevent heat generated by the first heat generator 11 from being transmitted to the second heat generator 12.

Note that the second heat generator 12 is cooled in such a manner that air, taken into the housing 2 from the inlet 3 by the operation of the exhaust fan 5, flows along the second heat generator 12 while flowing toward the outlet 4. The flow of the air along the second heat generator 12 is referred to as a second flow path F2 and indicated by an arrow of a two-dot chain line in FIGS. 3 and 4. The guide plate 21 is a member configured to make the first flow path F1 more distant from the second flow path F2 in the height direction.

As thus described, in the present embodiment, the guide plate 21 causes the first flow path F1 and the second flow path F2, through each of which air flows and moves, to reach the outlet 4 while being separate from each other in the height direction, the air cooling each of the first heat generator 11 and the second heat generator 12 which are the plurality of substrates disposed overlapping with each other in the height direction. Hence in the present embodiment, the first heat generator 11 and the second heat generator 12 are disposed overlapping with each other in the height direction, whereby it is possible to increase a density of the members disposed in the housing 2 and cool the first heat generator 11 and the second heat generator 12 effectively. Therefore, the endoscope apparatus 1 of the present embodiment can improve cooling performance of the plurality of heat generators disposed in the housing 2.

Second Embodiment

Figure 6:
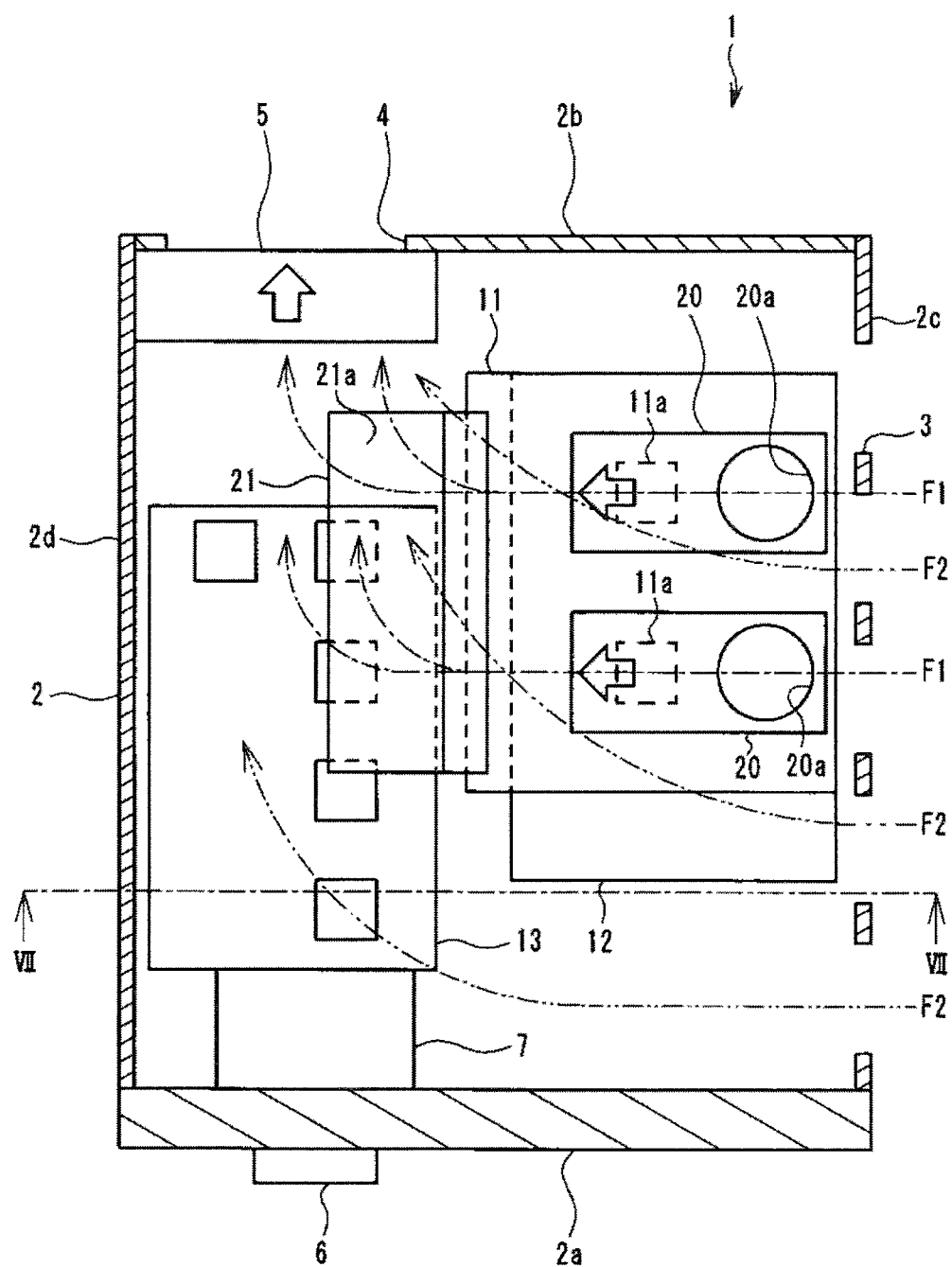
FIG. 6 is a view of an inside of a housing in a second embodiment, seen from above.
Figure 7:
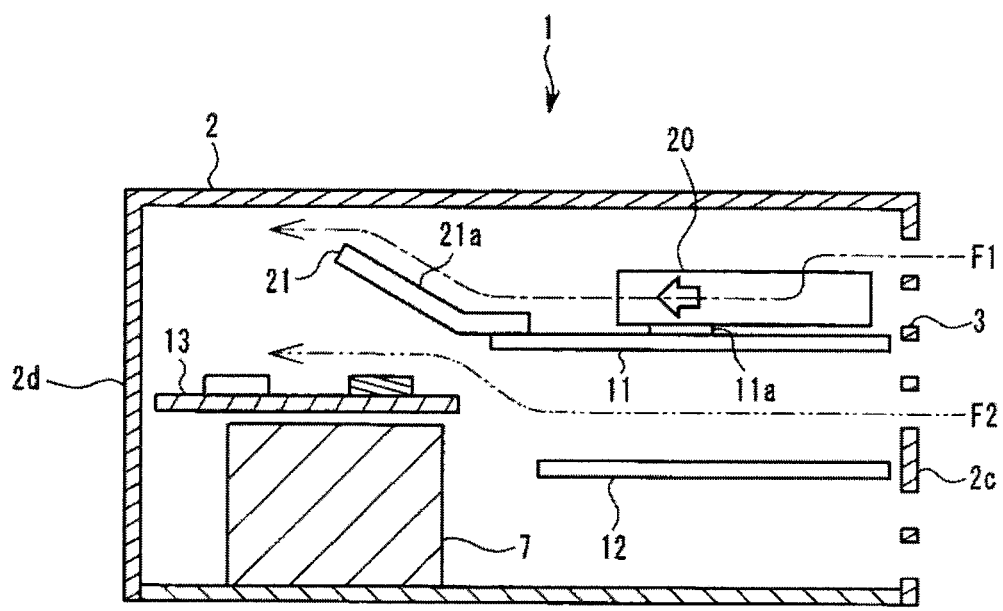
FIG. 7 is a sectional view taken along VII-VII of FIG. 6.

A second embodiment of the present invention will be described below. In the following, only a difference from the first embodiment will be described, components similar to the components in the first embodiment will be provided with the same numerals, and description of the components will be omitted as appropriate. FIG. 6 is a view of the inside of the housing 2 in the present embodiment, seen from above. FIG. 7 is a sectional view taken along VII-VII of FIG. 6.

The endoscope apparatus 1 of the present embodiment shown in FIGS. 6 and 7 is different from the first embodiment in that the inside of the housing 2 is provided with a third heat generator 13 configured to generate heat during operation of the endoscope apparatus 1.

In the present embodiment, as one example, the third heat generator 13 is a substrate formed with an electronic circuit configured to drive an LED and the like included in a light source apparatus 7. The light source apparatus 7 includes the LED, a condensing lens, a filter, and the like and emits illumination light to an optical fiber bundle included in the endoscope 100 connected to the connector portion 6.

Note that the third heat generator 13 may be divided into a plurality of substrates. Further, the third heat generator 13 is not limited to the substrates. For example, the third heat generator 13 may be a light source apparatus such as an LED or a member configured to generate heat such as an electric motor or may be a member such as a heat sink, through which heat generated by another member conducts.

The third heat generator 13 is separated from the first heat generator 11 and the second heat generator 12 and is disposed in such positions between the second heat generator 12 and the right side surface 2d as to at least partially overlap with the guide plate 21 in the height direction of the housing in order to at least partially overlap with the guide plate 21 when seen from above. In the present embodiment shown, the third heat generator 13 is disposed above the second heat generator 12 and below the first heat generator 11 in the height direction.

In the endoscope apparatus 1 of the present embodiment, the third heat generator 13 is disposed below the guide plate 21 in the same manner as in the first embodiment. Therefore, also in the present embodiment, the first flow path F1 is made more distant in the height direction from the second heat generator 12 and the third heat generator 13 downstream from the first heat generator, whereby it is possible to prevent high-temperature air after cooling the first heat generator 11, which flows through the first flow path F1, from flowing into peripheries of the second heat generator 12 and the third heat generator 13 and prevent heat generated by the first heat generator 11 from being transmitted to the second heat generator 12 and the third heat generator 13.

Further, in the present embodiment, the guide plate 21 and the third heat generator 13 are disposed so as to overlap with each other in the height direction of the housing in order to at least partially overlaps with the guide plate 21 when seen from above, thereby enabling an increase in density of the members disposed in the housing 2. As described above, the endoscope apparatus 1 of the present embodiment can improve the cooling performance of the plurality of heat generators, while increasing the density of the members disposed in the housing 2.

Third Embodiment

Figure 8:
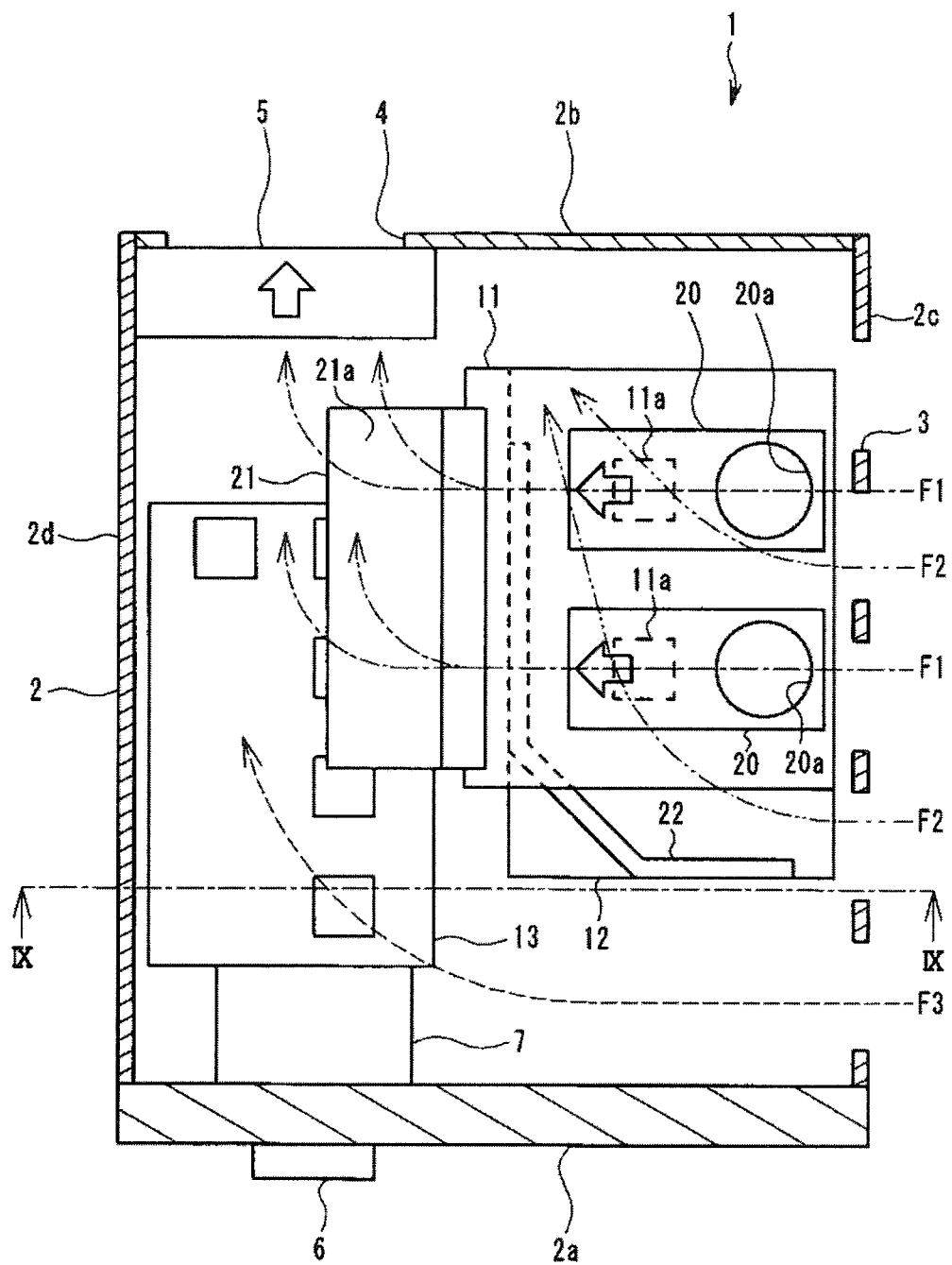
FIG. 8 is a view of an inside of a housing in a third embodiment, seen from above.
Figure 9:
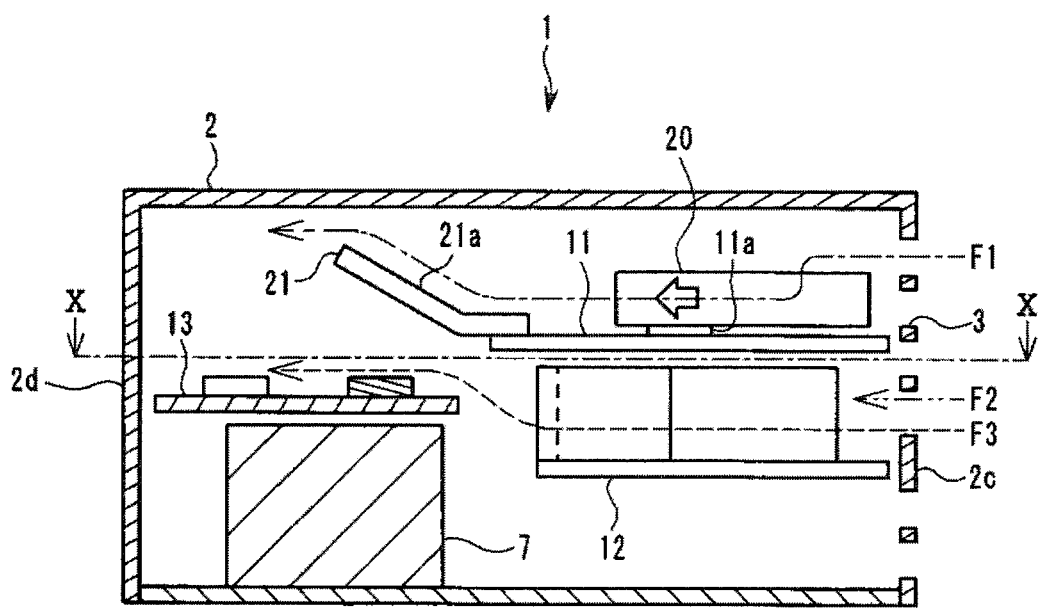
FIG. 9 is a sectional view taken along IX-IX of FIG. 8.
Figure 10:
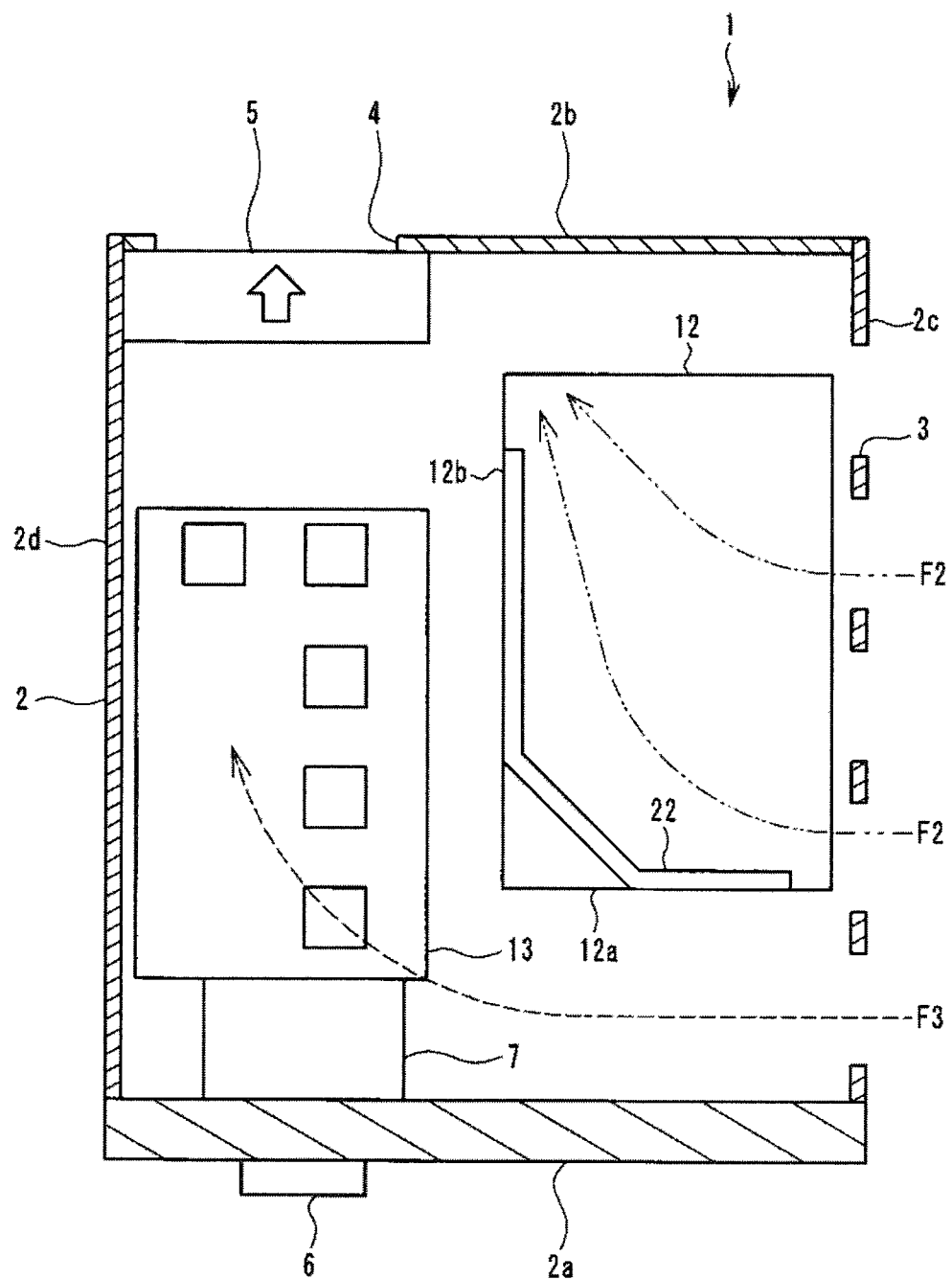
FIG. 10 is a sectional view taken along X-X of FIG. 9.

A third embodiment of the present invention will be described below. In the following, only a difference from the second embodiment will be described, components similar to the components in the second embodiment will be provided with the same numerals, and description of the components will be omitted as appropriate. FIG. 8 is a view of the inside of the housing 2 in the present embodiment, seen from above. FIG. 9 is a sectional view taken along IX-IX of FIG. 8. FIG. 10 is a sectional view taken along X-X of FIG. 9.

The endoscope apparatus 1 of the present embodiment shown in FIGS. 8 to 10 is different from the second embodiment in that a flow path division portion 22 is provided inside the housing 2.

The flow path division portion 22 is a wall-shaped member disposed upright at a height between the first heat generator 11 and the second heat generator 12 and configured to horizontally divide a flow path for air into the second flow path F2 and a third flow path F3, the air flowing and moving at a height between the first heat generator 11 and the second heat generator 12 in the housing 2 by operation of the exhaust fan 5 so as to reach the outlet 4 from the inlet 3. The second flow path F2 is a path for air which is taken into the housing 2 from the inlet 3 and thereafter passes in a vicinity of the second heat generator 12 to reach the outlet 4, and the third flow path F3 is a path for air which is taken into the housing 2 from the inlet 3 and thereafter passes in a vicinity of the third heat generator, while avoiding the second heat generator 12, to reach the outlet 4. In FIG. 10, the third flow path F3 is indicated by an arrow of a broken line.

More specifically, the flow path division portion 22 is a wall-shaped member which is disposed at the height between the first heat generator 11 and the second heat generator 12 in the housing 2, so as to surround at least part of a region 12a facing the front surface 2a side and a region 12b facing the right side surface 2d side on the periphery of the second heat generator 12 when seen from above, as shown in FIG. 10. In the present embodiment shown, the second heat generator 12 is a rectangular substrate when seen from above, and the flow path division portion 22 is a substantially L-shaped wall provided standing in the height direction along an outer side which faces the front surface 2a side of the second heat generator 12 in a rectangular shape and along an outer side which faces the right side surface 2d.

In the present embodiment, by providing the flow path division portion 22, it is possible to prevent relatively high-temperature air after cooling the second heat generator 12 from flowing into the periphery of the third heat generator 13 and to cause air with a small temperature rise after being taken into the housing 2 to flow and move in the vicinity of the third heat generator 13.

In the present embodiment, similarly to the first embodiment, the first flow path F1 passing in the vicinity of the first heat generator 11 is made more distant in the height direction from the second heat generator 12 and the third heat generator 13 downstream from the first heat generator, whereby it is possible to prevent high-temperature air after cooling the first heat generator 11, which flows through the first flow path F1, from flowing into the peripheries of the second heat generator 12 and the third heat generator 13.

Therefore, the endoscope apparatus 1 of the present embodiment can improve the cooling performance of the plurality of heat generators, while increasing the density of the members disposed in the housing 2.

Fourth Embodiment

Figure 11:
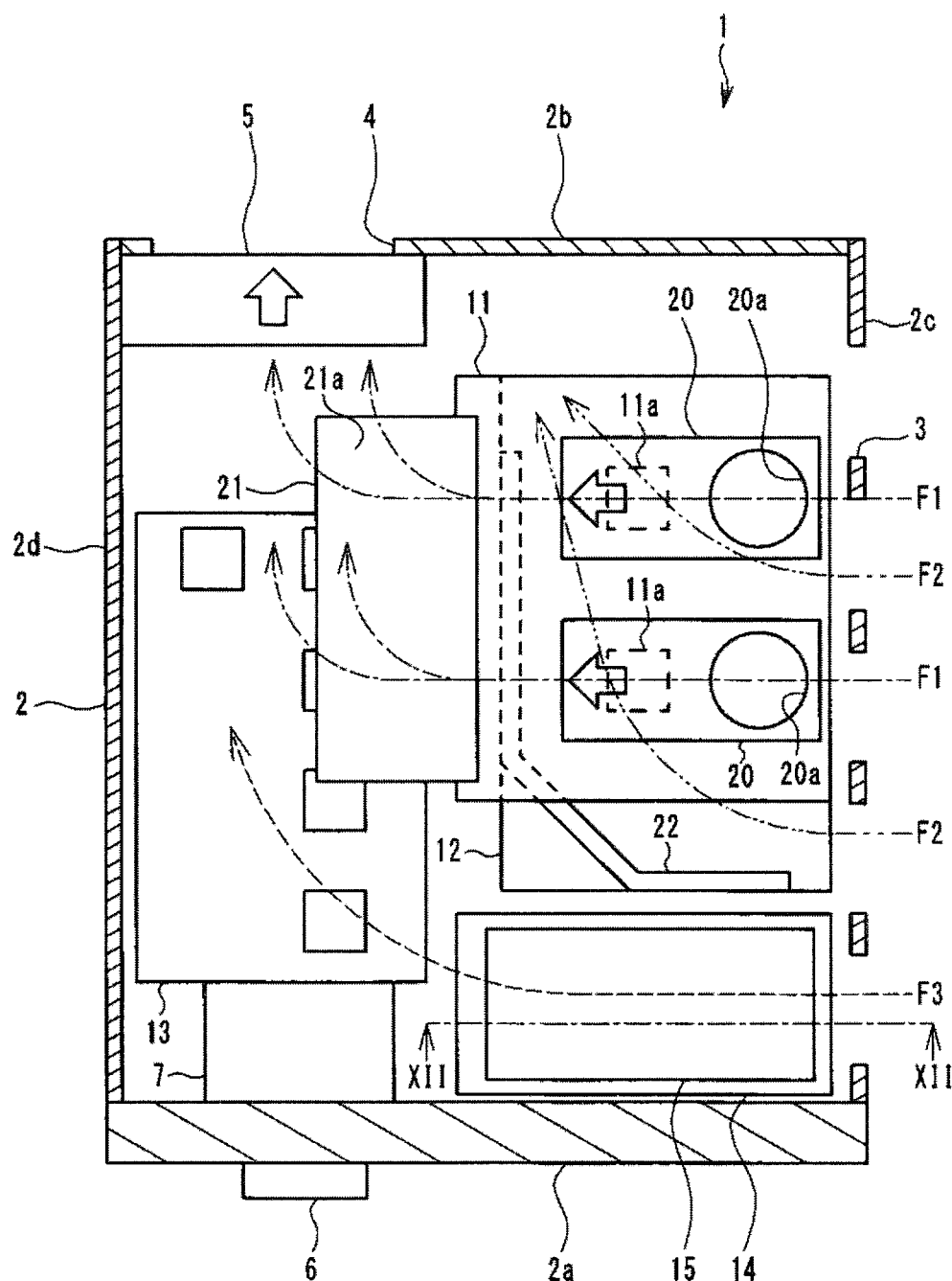
FIG. 11 is a view of an inside of a housing in a fourth embodiment, seen from above.
Figure 12:
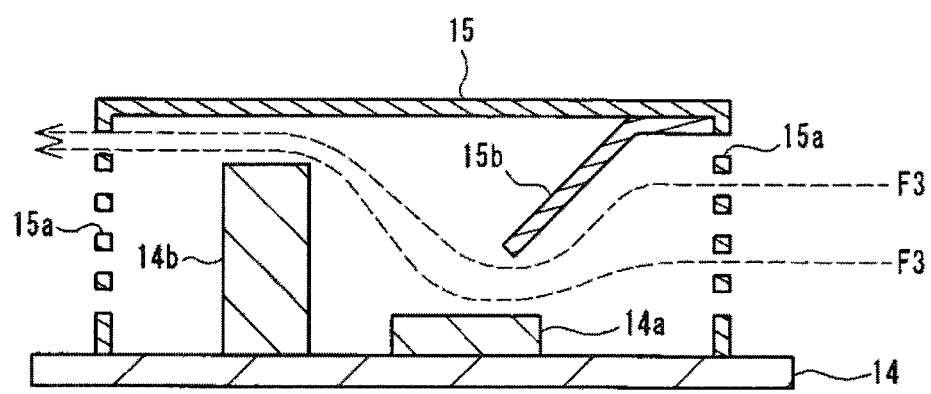
FIG. 12 is a sectional view taken along XII-XII of FIG. 11.

A fourth embodiment of the present invention will be described below. In the following, only a difference from the third embodiment will be described, components similar to the components in the third embodiment will be provided with the same numerals, and description of the components will be omitted as appropriate. FIG. 11 is a view of the inside of the housing 2 in the present embodiment, seen from above. FIG. 12 is a sectional view taken along XII-XII of FIG. 11. In FIG. 11, an upper part of the figure is an upper part of the endoscope apparatus 1.

The endoscope apparatus 1 of the present embodiment shown in FIGS. 11 and 12 is different from the third embodiment in that a shielded substrate 14 is provided inside the housing 2.

The shielded substrate 14 is a substrate formed with an electronic circuit that is covered with a metal electromagnetic shielding member 15. The shielded substrate 14 is formed with an electronic circuit configured to generate a drive signal of the image pickup apparatus 110 that is connected via the connector portion 6, for example. As shown in FIG. 12, the electromagnetic shielding member 15 is a member having the shape of a rectangular parallelepiped box and configured to cover an upper surface of the shielded substrate 14 on which electronic components are mounted.

The shielded substrate 14 is disposed so as to have an upper surface substantially horizontal between the second heat generator 12 and the front surface 2a and is disposed such that the electromagnetic shielding member 15 is located above the third flow path F3.

A plurality of opening portions 15a, which are through holes, are formed on each of side surfaces of the electromagnetic shielding member 15 which face upstream and downstream of the third flow path F3. Note that the opening portion 15a may be formed on another side surface of the electromagnetic shielding member 15. Due to provision of the opening portions 15a on the side surfaces of the electromagnetic shielding member 15, part of the air flowing and moving along the third flow path F3 in the housing 2 passes in the electromagnetic shielding member 15.

A guide wall 15b is provided inside the electromagnetic shielding member 15 of the present embodiment. The guide wall 15b has an inclined surface protruding from an upper surface inside the electromagnetic shielding member 15 and inclined downward toward the downstream of the third flow path F3.

In the present embodiment, due to provision of the guide wall 15b inside the electromagnetic shielding member 15, a region is formed where the air passing in the electromagnetic shielding member 15 passes in a vicinity of the upper surface of the shielded substrate 14 on which the electronic components are mounted. In the present embodiment, a heat generation unit 14a, which is an electronic component having a large quantity of heat, is disposed in a region in which the air passes through a vicinity of the shielded substrate 14 due to the existence of the guide wall 15b.

The height of the electromagnetic shielding member 15 in the box shape is determined to be a value with which the electromagnetic shielding member 15 avoids interference with a high member 14b having the largest height and mounted on the shielded substrate 14. For this reason, in the conventional technique where the guide wall 15b is not provided in the electromagnetic shielding member 15, the air may pass in an upper portion in the electromagnetic shielding member 15, which may cause deterioration in cooling efficiency of the heat generation unit 14a. In contrast, in the endoscope apparatus 1 of the present embodiment, the air can be caused to pass in the vicinity of the heat generation unit 14a in the electromagnetic shielding member 15 due to provision of the guide wall 15b, thereby enabling improvement in the cooling efficiency of the heat generation unit 14a. Further, improving the cooling efficiency of the heat generation unit 14a enables reduction in an opening area of the opening portion 15a provided in the electromagnetic shielding member 15, whereby it is possible to improve performance of electromagnetic shielding exerted by the electromagnetic shielding member 15.

Note that the present invention is not limited to the embodiments described above, and can be modified as appropriate in a scope not contrary to the gist or the concept of the invention readable from the whole claims and specification, and an endoscope apparatus involving such a modification is also included in the technical scope of the present invention.

What is claimed is:

1. An endoscope apparatus comprising:
    a housing;
    an inlet configured to take external air into the housing;
    an outlet configured to exhaust air in the housing to outside of the housing, wherein a surface of the housing parallel to the outlet intersects a surface of the housing parallel to the inlet;
    a first heat generator disposed in the housing and configured to generate heat;
    an air feeding unit disposed in the housing and configured to cause air for cooling the first heat generator in a vicinity of the first heat generator to pass in a direction intersecting the surface of the housing parallel to the inlet;
    a second heat generator disposed in the housing and provided in a place below a flow path for the air, caused by the air feeding unit to pass in the vicinity of the first heat generator, in a height direction of the housing; and
    a guide plate provided on the flow path for the air, caused by the air feeding unit to pass in the vicinity of the first heat generator, and having an inclination for changing the flow path for the air after passage in the vicinity of the first heat generator to a place above in the height direction of the housing.

2. The endoscope apparatus according to claim 1, wherein
    the second heat generator is provided below the flow path for the air, caused by the air feeding unit to pass in the vicinity of the first heat generator, in the height direction of the housing and has a quantity of heat smaller than a quantity of heat of the first heat generator, and
    the guide plate changes the flow path for the air, caused by the air feeding unit to pass in the vicinity of the first heat generator, upward in the height direction of the housing.

3. The endoscope apparatus according to claim 1, comprising a third heat generator at least partially overlapping with the guide plate when seen from above, disposed below the guide plate, and configured to generate heat.

4. The endoscope apparatus according to claim 3, wherein
    the third heat generator is disposed at a height between the first heat generator and the second heat generator in the housing, and
    the device further comprises a flow path division portion provided between the second heat generator and the third heat generator and configured to divide the air reaching the outlet from the inlet into a flow path configured to cause the air taken in from the inlet to pass in a vicinity of the second heat generator and a flow path configured to cause the air taken in from the inlet to pass in a vicinity of the third heat generator.

5. The endoscope apparatus according to claim 3, wherein
    the first heat generator, the second heat generator, and the third heat generator are substrates, and
    the air feeding unit is a fan provided on the first heat generator.

* * * * *